United States Patent [19]

Brunger et al.

[11] Patent Number: 5,560,962
[45] Date of Patent: Oct. 1, 1996

[54] STRUCTURE HAVING CONTROLLED WATER RESISTANCE

[75] Inventors: Peter M. Brunger, Stockton On Tees; David J. Kemmish, Yorkshire, both of United Kingdom

[73] Assignee: Zeneca Limited, London, England

[21] Appl. No.: 204,263

[22] PCT Filed: Nov. 11, 1992

[86] PCT No.: PCT/GB92/02078

§ 371 Date: Aug. 10, 1994

§ 102(e) Date: Aug. 10, 1994

[87] PCT Pub. No.: WO93/10308

PCT Pub. Date: May 27, 1993

[30] Foreign Application Priority Data

Nov. 12, 1991 [GB] United Kingdom ............. 9123997

[51] Int. Cl.$^6$ ............... B05D 1/06; B05D 1/24; A61F 13/15
[52] U.S. Cl. .................. 427/478; 427/185; 604/367
[58] Field of Search .................. 427/384, 394, 427/458, 475, 185; 604/367, 370; 428/286, 290

[56] References Cited

U.S. PATENT DOCUMENTS

| | | | |
|---|---|---|---|
| 3,107,172 | 10/1963 | Baptist et al. | 106/160 |
| 3,657,044 | 4/1972 | Singer . | |
| 4,009,313 | 2/1977 | Crawford et al. | 428/290 |
| 4,503,098 | 3/1985 | Potts | 427/394 |
| 4,826,493 | 5/1989 | Martini et al. | 604/327 |

FOREIGN PATENT DOCUMENTS

| | | | |
|---|---|---|---|
| 0306799 | 3/1989 | European Pat. Off. | B05D 1/06 |
| WO91/13207 | 9/1991 | WIPO | D21H 19/62 |
| WO92/01733 | 2/1992 | WIPO | C08J 3/02 |

*Primary Examiner*—Shrive Beck
*Assistant Examiner*—Fred J. Parker
*Attorney, Agent, or Firm*—Cushman Darby & Cushman, L.L.P.

[57] ABSTRACT

A structure of controlled water resistance comprises a core of material having mechanical strength when dry but not when water-wet and a coating comprising biodegradable water resistant polymer. The polymer is preferably applied to the core by electrostatic coating of dry fine particles as laid down in microorganism cells or as clusters of such particles. The structure is useful in the form of disposable biodisintegrable articles.

6 Claims, No Drawings

STRUCTURE HAVING CONTROLLED WATER RESISTANCE

BACKGROUND OF THE INVENTION

THIS INVENTION relates to a structure having controlled water resistance and in particular to a structure having a water-disintegrable core and a water-resistant biodegradable coating.

SUMMARY OF THE INVENTION

The invention provides a structure comprising a core of a material having mechanical strength when dry but not when water-wet and a coating comprising biodegradable water-resistant polymer.

It provides also compound structures in which two or more structures are laminated together or in which core material or other material is laminated to the structure.

The core can be for example a foam or assemblage of particles or assemblage of fibres or any combination of these. Such fibres are preferably naturally occurring, rather than man made. The core thus could be bread-like or paper or papier-maché or felt or candyfloss-like. It may include one or more water-sensitive and/or biodegradable adhesives. There may be water-resistant material mixed in with water-disintegrable material, provided the proportion thereof is insufficient to decrease water-sensitivity below the level required for the intended use of the structure.

The coating can be, or can be convertible by heat treatment to, for example a smooth fused or sintered film covering the whole surface of the core, or a reticulated film following the contours of the core, or both. It can be limited, for example to the surfaces of the units (such as fibres) of which the core is composed, or to junctions between such units. The coating can be of thickness in the range 5 to 500 preferably 20 to 200 μm, for example. The coating of biodegradable polymer can be additional to a coating of water-sensitive material.

DESCRIPTION OF THE PREFERRED EMBODIMENTS

In one form of the invention the structure has one dimension substantially less than the other two, so that it has two sides: then it can carry the coating on both sides or only one side. The polymer coating can be the working surface of the structure. Alternatively the core material can be the working surface, for example, in a structure required to absorb water or grease from one side while the other side maintains its mechanical integrity during absorption. Such structures are subject to disintegration thereafter in a microbially active environment.

The structure is when dry preferably rigid or to a required extent flexible and resilient, e.g. to permit rolling-up.

The coating is for example the product of applying the polymer in fine particulate form, followed by heating to fuse or sinter the polymer and, if appropriate, to increase its crystallinity.

The material of the core can be for example water-soluble, for example sugar, starch, polyvinyl alcohol or a water-sensitive ester or ether thereof or poly(meth) acrylic acid or a water-sensitive ester or amide thereof or a cationic vinyl or (meth)acrylic polymer. It may be slowly biodegradable, such as cellulose, eg wood pulp or paper, or non-delignified material such as wood shavings, sawdust, hay or straw. Very suitably it is paper or papier maché, especially recycled. For practical purposes it is thus to be regarded as at least water-disintegradable.

The material of the coating preferably comprises at least one polyester, especially a polyhydroxyalkanoate. Particular examples of polyhydroxyalkanoates are those consisting of repeating units of formula O-R-CO where R is an aliphatic chain of 2 to 6 carbon atoms optionally carrying a lower alkyl ($C_1$–$C_4$) branch particularly on the carbon atom next to oxygen in the chain. Their molecular weight Mw is preferably over 100,000, especially in the range 200,000 to 1.5 million. In particular examples, referred to hereinafter as HB(HV), the units are

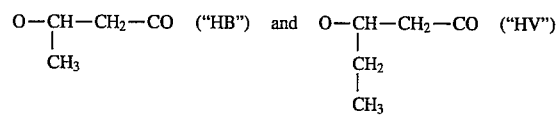

or both such units may be present in the polyester. The relative proportion of such units is preferably such as will give a polymer that is crystallisable e.g. on holding at 20° to 100° C. for 0.1 to 0.5 h or possibly up to 4 h. If copolymer is used it may contain for example at least 2, especially 3 to 25, mol percent of HV, balance HB. The proportion of HB and HV units may if desired be attained by blending for example polyester containing 0–5 mol % HV with polyester containing 5–30% HV.

These proportions disregard very small, possibly fractional, percentages of units containing more than 5 carbon atoms, which may be present. The references to "HB" and "HV" represent abbreviations for hydroxybutyrate and hydroxyvalerate, i.e. the residue of 3-hydroxy butyric acid and 3-hydroxy valeric acid, respectively.

The material of the coating may consist of such polyester or may be a blend with other polymer. The proportion of other polymer in the blend depends on how rapidly the coating is required to biodegrade, and on the extent to which the other polymer is itself biodegradable or biodisintegrable. Suitable blends are described in our EP-A-0052460 and PCT application 91/01733 claiming priority from GB application 9016345.2 filed Jul. 25, 1990.

In addition to polymer(s) there may be present any of the usual polymer processing additives, for example one or more plasticisers, particulate fillers, reinforcing fibres, pigments and nucleating agents, subject to suitability for the method used for making the structure.

The invention in a second aspect provides a method of making the structure by the steps of (in either order, possibly more than once each) shaping the core material and applying to it the biodegradable polymer.

The core material may be shaped wet and then dried, or shaped dry with a fine-particulate fusible adhesive, then heat-set. Application of polymer is suitably to core material having a water content low enough for it to keep its shape during application, that is, in a "green" condition or more dry. It may be substantially dry, for example in equilibrium with ambient air at up to 90% relative humidity. If it contains an adhesive, the adhesive may be or include a biodegradable material, possibly a microbiologically produced polymer.

The applying operation uses polymer preferably in a dry fine particulate state. A very suitable particulate polymer is a polyhydroxyalkanoate, especially HB(HV) polymer as made microbiologically and recovered by one of the following processes:

(1) the procedure described in EP-A-46335 involving heating an aqueous suspension of micro-organism cells containing polymer granules under pressure to above 100° C., particularly to above 150° C., and then releasing the pressure. This process causes the cell walls to rupture enabling the polymer granules to be separated from the cell debris by conventional methods;

(2) digesting dried cells, obtained for example by spraying an aqueous cell suspension with hypochlorite, for example as described in J. Gen. Microbiol. 19 (1958) 198–209.

(3) breakage of the cells by methods such as treatment with acetone, followed by extraction of the polymer from the broken cells by treatment with a solvent in which the polymer is soluble. Examples of such processes are described in US-A-3036959 and 3044942 in which the solvents employed are pyridine or mixture of methylene chloride and ethanol. Other extraction solvents for the polymer in the form in which it is produced in the cells include cyclic carbonates such as 1,2-propylene carbonate (see US-A-4101533); chloroform (see US-A-3275610); and 1,2-dichloroethane (as disclosed in EP-A-15123). US-A-3275610 discloses other methods of cell breakage viz. ultrasonic vibration, grinding, French pressing, freezing/thawing cycles and lysozyme treatment, while as described in EP-A-15123, spray or flash drying of the suspension of cells as produced by culturing the micro-organism can also cause sufficient cell breakage to enable the polymer to be extracted from the cells. Polymer powder can be prepared from the solution of the polymer in the extraction solvent by, for example, spray drying the solution, to give a very fine powder;

(4) digestion of the non-HB(HV) polymer material in the micro-organism cells, for example with a proteolytic enzyme composition. In this way the non-HB(HV)polymer cell material can be solubilised, leaving the HB(HV) in particulate form. In order to assist separation of the polymer from the aqueous medium, the aqueous suspension is preferably heated, particularly to above 100° C., prior to the enzyme digestion;

(5) where necessary the particles of the HB(HV) polymer, eg spray dried powder, or agglomerates of granules, can be ground for the requisite particle size.

By processes (1), (2) and (3), polymer can be separated from the cell residue as granules as laid down in the cells or as clusters of such granules.

The microorganism producing the polymer can be any one of those capable of accumulating it, for example of the genera Alcaligenes, Athiorhodium, Azotobacter, Bacillus, Nocardia, Pseudomonas, Rhizobium and Spirillium, or others such as Escherichia or, alternatively a eukariote into which the necessary genetic material has been introduced. Alcaligenes, for example *A. eutrophus* or possibly *A. latus* is conveniently used.

The polymer used is preferably in particles of average size in the range 0.2 to 500, especially 0.5 to 200 μm. It is particularly advantageous that the polymer particles harvested from the micro-organism (in for example processes 1, 2 or 4) can be readily available within these size ranges. These ranges include particles as laid down in microorganism cells and also clusters of such particles such as result from the separation technique and/or from spray drying a latex or solution. If clusters are used, their particle size is suitably in the range 5–100, especially 10 to 80 μm.

The application operation may be by a dry method, for example dusting or fluidised bed immersion or spraying or electrostatic coating, or by a wet method for example doctoring or dip-coating or spraying of a latex of particles in water or of a solution in an organic liquid. It is an advantage of the dry or latex method that particles requiring little preparative treatment other than separation from cell debris can be used.

Electrostatic coating is preferably employed, especially by contacting the core with electrostatically charged polymer particles. This may be by immersion in a fluidised bed of such particles. If the core is to be coated on one side only, two cores may be sandwiched together before immersion, if their shape permits this. For electrostatic coating the core may be wet with water to facilitate earthing. Alternatively, a metal ground plate may be applied to the side or parts of the core that are not to be coated. If the core has 3-dimensional shape, the ground plate may be metal foil formed to its shape. However, coating can be successfully carried out without such earthing.

After application of polymer, the coated core may be stored or shipped. It is subjected preferably to one or both of the following heat treatments:

drying (1), if the core was wet or a wet application method was used;

setting (2), typically at 160° to 200° C. for 0.1 h;

lamination (3), if a multi-layer structure is required. crystallisation, typically at 40° to 75° C. for 0.1 to 1 h, possibly in contact with a solid surface such as a calender. Such surface may be for example mirror-polished, textured, profiled or embossed with a message, or may merely act as a heat transfer medium.

The polymer coating after setting (2) can be tacky, or become tacky in the next following treatment, sufficiently for lamination (3) without further adhesive, but further adhesive can be used if desired, preferably biodegradable or discontinuously applied.

The invention provides a process and apparatus in which these operations are performed successively on a continuous web of core material, or in combination with an initial step of shaping or part-shaping, and drying if such initial step is of wet material.

In a third aspect the invention provides particular examples of the structure, namely boards, sheets and dishes coated on one or both sides; vessels and pipes;

blanks to be heat set or crystallised or both;

blanks to be slit or chopped;

stripform or particulate litter or absorbent packing;

packaging, especially compartmented trays for water- or grease- containing foods;

personal hygiene products such as diapers, sanitary napkins, incontinence sheets or surgical swabs;

ostomy bags;

bed pans, urine bottles; or any of these carrying a layer of core or polymer material on one or both sides.

Such structures preferably are disintegrable rapidly enough to be handled by domestic or hospital sewerage or wet waste disposal machines and composting systems and plants. They are capable of many duties now performed by foamed polystyrene, but in a more environmentally acceptable way.

EXAMPLE 1 (Design)

For an experimental run the core is a pressed papier maché dish and the coating material is a polymer consisting of HB and HV units in the mol ratio 94 to 6 and having a molecular weight of over 200,000, preferably over 350,000.

It was produced by spray drying an aqueous suspension resulting from the removal of cell debris from micro organism cells and had an average particle diameter of about 50 μm.

The powder is charged to an Electrostatic Fluidised Bed Coater (Electrostatic Technology Inc, Branford, Conn. USA) and applied to outer side of the dish at coating weights corresponding (after the heat treatments to be described) to about 100 and about 25 μm thickness. The dish is removed from the Coater to an air oven at 180° C. and kept at 180° C. for a few minutes until the surface particles have fused together into a coherent film. The coated dish is then transferred to an air oven at 60° C. and kept there for 4 min until the polymer coating has crystallised.

From the results of dummy experiments preceding the above run it is expected that the dish will hold water for 5–10 min without collapsing and can then be disintegrated in sewerage, composting and other microbially active systems.

This was in fact confirmed. An egg carton coated on the outside was found to float on water for at least 10 h. The corresponding uncoated control sank in about 10 min.

EXAMPLE 2

Coating runs were carried out using a variety of core materials and microbiologically produced polyester of molecular weight Mw 643,000 consisting of HB and HV units in the mol ratio 93 to 7 in the form of particles passing a 35 ASTM sieve but 98.6% by weight greater than 300 mesh. The polymer was applied using a Model C30 mini coater from the range of coaters mentioned in Example 1, operated in these conditions:

| | |
|---|---|
| Fluidised bed air velocity | 5.66 $m^3$ $min^{-1}$ |
| Kilovolt setting | 80 |
| Immersion time | 4, 6 or 8 sec | to weighed core specimens backed by a metal ground plate. The coated specimens were weighed, then heated at 180° C. for 2 min to fuse the coating and at 60° C. for 5 min to permit crystallisation, then tested for water resistance by observing whether one drop of water on the coating for one minute soaked in or not. Results for typical core materials are shown in Table 1.

TABLE 1

| Core Material | Wt % polyester applied | Water Resistance | Surface Quality |
|---|---|---|---|
| Kraft Paper | 97.5 | Yes | moderately rough |
| Kraft Paper | 55.6 | Yes | moderately rough |
| Egg board (papier maché) | 44.4 | Yes | rough |
| Egg board (papier maché) | 17.0 | Yes | rough |

The coated specimens are ready for use as for example disposable water-containing vessels. If smoothness is required the coating may be calendered or otherwise smoothed.

EXAMPLE 3

Example 2 was repeated using a polyester consisting of HB and HV units in the mol ratio 81 to 19 and having Mw 678,000. Owing to slow crystallisation the coated specimens were held at ambient temperature for 1 h before testing. Results for typical core materials are shown in Table 2.

TABLE 2

| Core Material | Wt % polyester applied | Water Resistance | Surface Quality |
|---|---|---|---|
| Kraft paper | 244.4 | Yes | moderately rough |
| Egg board (papier maché) | 95.0 | Yes | rough |
| Fibreglass Cloth | 20.8 | Not Tested | Smooth |

EXAMPLE 4

The procedure of Example 2 was repeated using polyester consisting of HB and HV units in the mol ratio 83 to 17. For a single core material (papier maché egg carton) the following variables were explored:

(a) effect of aluminium foil earth pressed to egg carton contour;

(b) effect of immersion time 4, 6 or 8 sec;

(c) effect of kilovolt setting.

For each coating operation the air flow rate was 5.1 $m^3$ $min^{-1}$. Crystallisation was apparently complete within 10 min at 60° C.

A representative selection of the coating weights obtained is shown in Table 3.

TABLE 3

| Aluminium Foil Earth | Immersion time, sec | Kilovolt setting | Coating by weight |
|---|---|---|---|
| − | 4 | 60 | 45.7 |
| + | 4 | 60 | 38.2 |
| − | 4 | 50 | 30.8 |
| − | 6 | 50 | 42.8 |
| − | 8 | 50 | 52.3 |
| − | 4 | 40 | 8.0 |
| − | 4 | 50 | 30.8 |
| − | 4 | 60 | 29.7 |
| − | 4 | 70 | 40.1 |
| − | 4 | 80 | 62.3 |

By visual examination the optimal coating weight was 30–50%: such specimens could be flexed without cracking the coating, had a uniform appearance and resisted penetration by a water drop for at least 1 min. The lower coating weight obtained using the aluminium foil earth is attributed to preferential attraction of smaller particles.

EXAMPLE 5: Triboelectric coating

Pressed papier maché sheets 120×70 mm×1.25 mm were coated on one side with polymer consisting of HB and HV units in the mol ratio 84.4 to 15.6 having Mw 646,000, melt flow index 10 at 190° C. using a Davenport MFI Grader, and peak melting point 145° C. as calculated using a Perkin ELmer DSC4 instrument.

The polymer, in the form of powder produced by spray drying an aqueous suspension resulting from the removal of cell debris from *A. eutrophus* cells, was sieved to a particle size range 60–200 μm. It was placed in a small tank, fluidised by blowing air in from below, sucked from the fluidised bed by a Venturi effect and blown along a plastic tube into the inlet of a Ransburg Gema triboelectric gun. Within the gun the particles acquired electrostatic charge by frictional contact with PTFE (polytetrafluoroethylene) surfaces. The emerging powder was directed onto the papier mâché sheets hanging in an earthed frame. A range of spray times in the range 5 to 30 sec was used, to provide a range of coating weights. The sprayed sheets were cured in a fan-assisted oven at 200° C. for 20 min, then held at 60° C. for 4 min to permit crystallisation. The water-proofing effectiveness of the coating was tested by placing a drop of Lugol's reagent (potassium iodide+iodine in aqeous ethanol) on it and noting the time taken for absorption to occur. Typical coating weights were in the range 45 to 200 g m$^{-2}$ and absorption times 30 to 125 min.

We claim:

1. A method for making a structure comprising a fibrous assembly core having mechanical strength when dry but not when water-wet and a coating comprising a water-resistant polymer, said method comprising electrostatically applying dry particles of the water-resistant polymer to at least one exterior surface of said core, in which the water-resistant polymer is a biodegradable microbiologically produced polyhydroxyalkanoate consisting of repeating units of formula O-R-CO where R is an aliphatic chain of 2 to 6 carbon atoms optionally carrying a $C_1$–$C_4$ branch on the carbon atom next to oxygen in the polymer chain; and the particles of the water-resistant polymer are in the size range 0.2 to 500 microns as laid down in microorganism cells or clusters of such particles, and are used after removal of cell debris.

2. A method according to claim 1 in which the core is of papier-mache.

3. A method according to claim 1 in which the applied particles are of average size in the range 0.5 to 200 microns and the coating is 20 to 200 microns thick.

4. A method according to claim 1 in which the polyhydroxyalkanoate contains 3 to 25 mol percent of hydroxyvalerate residues, the balance being hydroxybutyrate residues.

5. A method according to claim 1 which comprises forming a fluidized bed of said dry particles of water-resistant polymer and immersing said core in said fluidized bed.

6. A method according to claim 5 in which the structure has a 3-dimensional shape and there is applied to the core, before coating, a metal foil ground plate formed to said shape and applied to the parts of the core that are not to be coated.

* * * * *